US00PP10373P

United States Patent [19]

Barnhoorn

[11] Patent Number: Plant 10,373

[45] Date of Patent: May 5, 1998

[54] HIPPEASTRUM (AMARYLLIS) PLANT NAMED 'ROZETTA'

[75] Inventor: Andre Barnhoorn, Wilgespruit, South Africa

[73] Assignee: Hadeco (Pty.) Ltd., Maraisburg, South Africa

[21] Appl. No.: 671,567

[22] Filed: Jun. 28, 1996

[51] Int. Cl.[6] ..... A01H 5/00

[52] U.S. Cl. ..... Plt./68.1

[58] Field of Search ..... Plt./87.4, 68.1

*Primary Examiner*—Howard J. Locker
*Assistant Examiner*—Kent L. Bell
*Attorney, Agent, or Firm*—C. A. Whealy

[57] ABSTRACT

A distinct cultivar of Hippeastrum (Amaryllis) plant named 'Rozetta', characterized by its double flowers; unique medium pink tepal color with white midrib and narrow reddish veins; multiple flower scapes per bulb; relatively compact plant habit; and early flowering.

1 Drawing Sheet

The present invention relates to a new and distinct cultivar of Amaryllis plant, botanically known as *Hippeastrum hybrida*, and hereinafter referred to by the cultivar name 'Rozetta'.

The new cultivar is a product of a planned breeding program conducted by the inventor in Maraisburg, South Africa. The objective of the breeding program was to create new Amaryllis cultivars that were suitable for 15-cm container production, flowered quickly, with multiple flower scapes and attractive flower color.

The new cultivar originated from a cross made by the inventor of the *Hippeastrum hybrida* cultivar 'Double Beauty' (not patented) as the male or pollen parent with the *Hippeastrum hybrida* cultivar 'Safari' (not patented) as the female or seed parent.

The cultivar 'Rozetta' was discovered and selected by the inventor in 1987 as a flowering plant within the progeny of the stated cross in a controlled environment in Maraisburg, South Africa. Asexual reproduction of the new cultivar by double scaling at Maraisburg, South Africa, has shown that the unique features of this new Amaryllis are stable and reproduced true to type in successive generations.

The cultivar 'Rozetta' has not been observed under all possible environmental conditions. The phenotype may vary somewhat with variations in environment such as temperature and light intensity, without, however, any variance in genotype. The following observations, measurements and comparisons describe plants grown in Maraisburg, South Africa, under commercial practice in a fiberglass-covered greenhouse with average day/night temperatures of 24° C. and light levels of 2,000 lux.

The following traits have been repeatedly observed and are determined to be the unique characteristics of 'Rozetta'. These characteristics in combination distinguish 'Rozetta' as a new and distinct cultivar:

1. Double flowers.
2. Unique medium pink tepal color with white midrib and narrow reddish veins.
3. Multiple flower scapes per bulb.
4. Typically four flowers per umbel or scape that develop simultaneously.
5. Relatively compact plant habit, appropriate for 15-cm containers.
6. Quick to flower.

'Rozetta' is different from its pollen parent, the cultivar 'Double Beauty', in the following characteristics:

1. Plants of the cultivar 'Rozetta' have more flowers per flower scape than plants of the cultivar 'Double Beauty'.
2. Tepal color of plants of the cultivar 'Rozetta' is medium pink with white midrib and narrow red veins whereas the tepal color of plants of the cultivar 'Double Beauty' is mainly white with pink midrib and broad reddish veins.

'Rozetta' is different from its seed parent, the cultivar 'Safari', in the following characteristics:

1. Plants of the cultivar 'Rozetta' have fully double flower whereas plants of the cultivar 'Safari' have single flowers.
2. Plants of the cultivar 'Rozetta' are about 15 cm shorter than plants of the cultivar 'Safari'.
3. Overall tepal color of plants of the cultivar 'Rozetta' is medium pink whereas the tepal color of plants of the cultivar 'Safari' is red.

Plants of the cultivar 'Rozetta' are most similar in tepal color to the cultivar 'Summertime' (not patented). However, in side-by-side comparisons conducted in Maraisburg, South Africa, plants of the two cultivars are different in the following characteristics:

1. Overall tepal color of plants of the cultivar 'Rozetta' is a warmer pink, 50C, than the tepal color, 55A, of plants of the cultivar Summertime.
2. Plants of the cultivar 'Rozetta' have fully double flower whereas plants of the cultivar 'Summertime' have single flowers.

The accompanying colored photograph illustrates the overall appearance of the new cultivar, showing the colors as true as it is reasonably possible to obtain in colored reproductions of this type. The photograph comprises a side perspective view of a typical potted plant of 'Rozetta' grown in Maraisburg, South Africa.

In the following description, color references are made to The Royal Horticultural Society Colour Chart except where general terms of ordinary dictionary significance are used. Measurements and numerical values represent averages for typical plants in 15-cm containers.

Botanical classification: *Hippeastrum hybrida* cultivar 'Rozetta'.

Parentage:

*Male or pollen parent.*—*Hippeastrum hybrida* cultivar 'Double Beauty' (not patented).

*Female or seed parent.*—*Hippeastrum hybrida* cultivar 'Safari' (not patented).

Propagation:

*Propagation method.*—Bulbs, double scaling. Double scaling is a scaling propagation technique that utilizes two scales joined together by a section of the basal plate. To propagate using this method, bulbs are cut longitudinally into segments that include a portion of the basal plate and two oppositely-orientated scale pairs.

*Rooting habit.*—Mature bulbs are lifted (harvested) and cured with primary roots attached. After curing, bulbs are planted into containers for flowering and develop secondary roots. Thickest secondary roots are about 8 mm in diameter and light tan, 161C, in color.

*Time to initiate secondary roots.*—14 days at 25° C. soil temperature.

Plant description:

*Form.*—Upright. Typically two flower scapes develop in synchrony with a complement of six leaves.

*Plant height at flowering.*—Relatively compact plant habit, from soil level to top of flowers, about 50 cm, appropriate for 15-cm containers.

*Vigor.*—Rapid growth rate.

*Crop time.*—After planting cured bulbs, plants typically flower within five weeks.

*Foliage description.*—Leaves strap-like, simple, opposite, symmetrical, usually six in number. Stiff keeled mid-rib imparts rigidity to leaf. Size: Length: About 55 cm. Width: About 4.5 cm. Shape: Linear. Apex: Acute. Margin: Entire. Texture: Smooth, glabrous. Venation pattern: Parallel. Color: Young foliage upper side: 145B. Young foliage under side: 145C. Mature foliage upper side: 137A. Mature foliage under side: 137C.

Flower Description:

*Flower type and habit.*—For 28-cm diameter bulbs, two flower scapes are typically formed. Larger bulbs may produce three scapes. One umbel per flower scape with four double flowers that are symmetrically arranged in a horizontal plane around the center of the umbel. Flowers typically open simultaneously.

*Natural flowering season.*—Spring.

*Flower longevity.*—At 22° C., individual flowers will last 7 days on the plant or if cut, 5 days. Flowers persistent.

*Fragrance.*—Very faint citrus-cucumber fragrance.

*Flower diameter.*—About 20 cm.

*Flower height.*—About 20 cm.

*Flower buds (just before tepal separation).*—Size: Length: 11 to 11.2 cm. Width: About 4.5 cm. Shape: Oblanceolate. Rate of opening: Typically flowers are fully open two days after tepals separate. Color: Main color: 37C. Base of tepals: 145B. Tip of tepals: 145B. Extreme edge of tepals: 47A.

*Tepals.*—Quantity and arrangement: Two and a half concentric whorls of tepals and tepal-like structures, typically 15 tepals/tepal-like structures per flower. The outer whorl of tepals is normal and designated "main tepals". The next whorl of tepal-like structures are fused with the filaments and designated "filament tepals". Anthers are visible at the tip of the filament tepals. The innermost ring is irregular in appearance. Pistils of single Amaryllis flowers consist of a style with a trilobate stigma. In plants of the new cultivar, the lobe separation extends down the style creating three style-like structures that are fused with tepal-like structures and designated "stylar tepals". Shape: Main and filament tepals: Five are broadly obovate and lowest tepal is oblanceolate. Tepals overlapping, but not fused. Stylar tepals: Irregular, overlapping, but not fused. Size (uppermost obovate tepal for each tepal whorl): Length: Main tepal: About 13 cm. Filament tepal: About 11.1 cm. Stylar tepal: About 10 cm. Width (uppermost obovate tepal for each tepal whorl): Main tepal: About 8 cm. Filament tepal: About 6.5 cm. Stylar tepal: About 4.5 cm. Apex: Apiculate. Margin: Entire. Texture: Glabrous, smooth, pleated and velvety. Color, when opening and mature: Upper side: Main tepal: Tip: 155C. Base: 149C. Overall: 50C. Filament tepal: Filament tepals have a more prominent white mid-rib that is flanked by a dark red stripe that fades through striations to the dominant pink tepal color. Anther at tip: 159A. Midrib: 155C. Stripe: 47B. Base: 149C. Overall: 50C. Stylar tepal: Base: 149C. Overall: 50C. Throat, all tepals and tepal-like structures: 154D. Under side, all tepals and tepal-like structures: Central area from base: 154D. Overall: 55D. Tube, all tepals and tepal-like structures: 154D. With further development, tepals and tepal-like structures fade to 186C, and after senescence, continue to fade to 186B.

*Scape.*—Quantity: For 28-cm diameter bulbs, two scapes are typically formed. Larger bulbs may produce three scapes. Aspect: Strong, erect, rigid, and upright. Length: About 40 cm. Texture: Glabrous. Color: With waxy bloom: 138C. Without waxy bloom: 145A. Base: Spots of 182A.

*Reproductive organs.*—Stamens fused to tepal-like structures. Anthers visible at the tip of filament tepals and vary in size. Ripening of the anther may induce curling of the filament tepal tip. Length: About 10 cm. Anthers: Shape: Linear. Color: 159A. Pollen color: Approximately 162B. Pistils: One pistil divided into three styles each fused to a tepal-like structure. Style: Length: 10 to 12 cm. Color: 155C. Stigma color: 155C. Ovary number: Three-celled.

Bulb description (after harvesting and curing, before planting).

*Size.*—Diameter: About 8.9 cm. Circumference: About 28 cm.

*Color.*—With brown tunic: 164C with 166B/166C watermarks. Tunic removed: 159D.

Disease resistance:

May be susceptible to Stagonospora fungi under high humidity conditions.

Seed production: Plants of the new Amaryllis do not produce seed as plants of the new Amaryllis are believed to be sterile.

It is claimed:

1. A new and distinct cultivar of Hippeastrum (Amaryllis) plant named 'Rozetta', as illustrated and described.

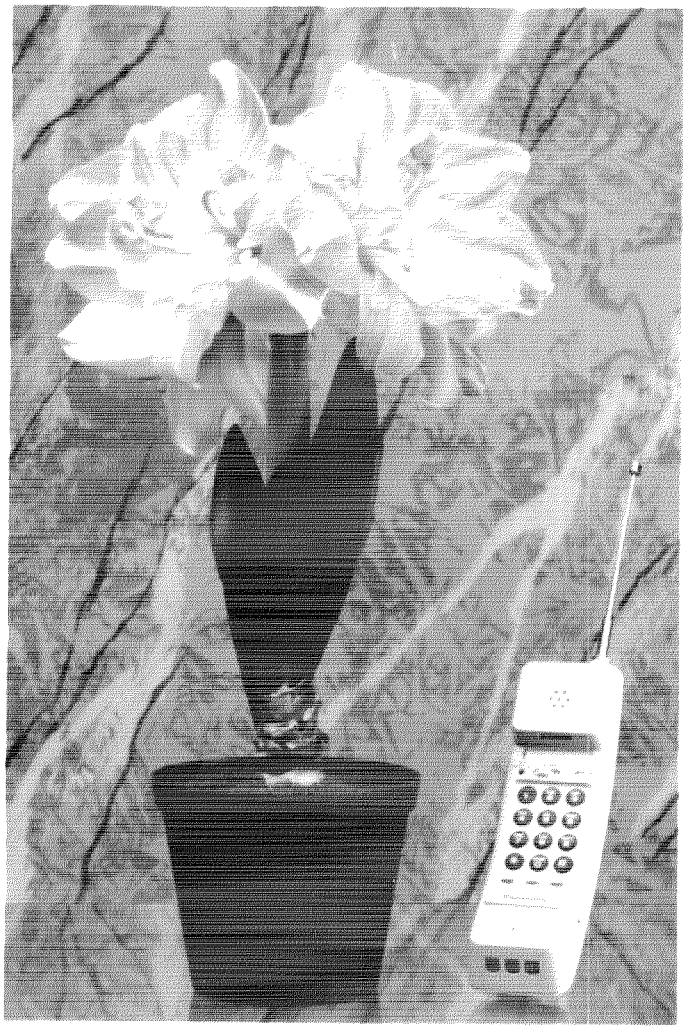

* * * * *